US010946029B2

United States Patent
Monari et al.

(10) Patent No.: US 10,946,029 B2
(45) Date of Patent: *Mar. 16, 2021

(54) DRY POWDER FORMULATION COMPRISING A CORTICOSTEROID AND A BETA-ADRENERGIC FOR ADMINISTRATION BY INHALATION

(71) Applicant: CHIESI FARMACEUTICI S.p.A., Parma (IT)

(72) Inventors: Elisa Monari, Parma (IT); Anna Maria Cantarelli, Parma (IT); Daniela Cocconi, Parma (IT); Irene Pasquali, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/015,666

(22) Filed: Jun. 22, 2018

(65) Prior Publication Data

US 2018/0296573 A1    Oct. 18, 2018

Related U.S. Application Data

(63) Continuation of application No. 14/417,484, filed as application No. PCT/EP2013/051187 on Jan. 23, 2013, now Pat. No. 10,028,964.

(30) Foreign Application Priority Data

Jan. 25, 2012    (EP) .................................... 12152392

(51) Int. Cl.
| | | |
|---|---|---|
| *A61K 31/573* | (2006.01) | |
| *A61K 9/14* | (2006.01) | |
| *A61K 31/167* | (2006.01) | |
| *A61K 31/20* | (2006.01) | |
| *A61K 47/26* | (2006.01) | |
| *A61P 11/00* | (2006.01) | |
| *A61P 11/06* | (2006.01) | |
| *A61M 15/00* | (2006.01) | |
| *A61K 9/00* | (2006.01) | |

(52) U.S. Cl.
CPC .......... *A61K 31/573* (2013.01); *A61K 9/0075* (2013.01); *A61K 9/14* (2013.01); *A61K 9/145* (2013.01); *A61K 31/167* (2013.01); *A61K 31/20* (2013.01); *A61K 47/26* (2013.01); *A61M 15/003* (2014.02); *A61M 15/009* (2013.01); *A61M 2202/064* (2013.01); *A61P 11/00* (2018.01); *A61P 11/06* (2018.01); *Y10S 514/826* (2013.01)

(58) Field of Classification Search
CPC .................................................... A61K 31/573
See application file for complete search history.

(56) References Cited

U.S. PATENT DOCUMENTS

| | | | |
|---|---|---|---|
| 6,645,466 B1 | 11/2003 | Keller et al. | |
| 8,778,402 B2 * | 7/2014 | Monari ..................... | A61K 9/14 424/489 |
| 9,402,825 B2 * | 8/2016 | Pasquali ............... | A61K 31/167 |
| 9,808,422 B2 * | 11/2017 | Pasquali ............... | A61K 31/167 |
| 10,028,964 B2 * | 7/2018 | Monari ..................... | A61K 9/14 |
| 2007/0202053 A1 * | 8/2007 | Bilzi ..................... | A61K 9/0075 424/46 |
| 2010/0055192 A1 * | 3/2010 | Musa ................... | A61K 9/0075 424/489 |
| 2011/0081301 A1 * | 4/2011 | Brambilla .............. | A61K 45/06 424/45 |
| 2011/0262543 A1 | 10/2011 | Cocconi et al. | |

FOREIGN PATENT DOCUMENTS

| | | | |
|---|---|---|---|
| EP | 1 312 357 | 5/2003 | |
| EP | 1 944 018 | 7/2008 | |
| EP | 1 982 709 | 10/2008 | |
| WO | 01/78693 | 10/2001 | |
| WO | 0178693 A2 | 10/2001 | |
| WO | WO-0178693 A2 * | 10/2001 | ........... A61K 9/0075 |
| WO | 02/28377 | 4/2002 | |
| WO | 2011/018532 | 2/2011 | |
| WO | 2011/120779 | 10/2011 | |
| WO | 2011/131663 | 10/2011 | |

OTHER PUBLICATIONS

R. Guchardi, et al. "International Journal of Pharmaceutics", vol. 348, No. 1-2, pp. 10-17 (2008).
International Search Report in PCT/EP2013/051187 dated May 5, 2013.

* cited by examiner

*Primary Examiner* — Isaac Shomer
(74) *Attorney, Agent, or Firm* — Oblon, McClelland, Maier & Neustadt, L.L.P.

(57) ABSTRACT

Compositions comprising a corticosteroid and a beta-adrenergic are useful for treating inflammatory or obstructive airways diseases.

12 Claims, No Drawings

DRY POWDER FORMULATION COMPRISING A CORTICOSTEROID AND A BETA-ADRENERGIC FOR ADMINISTRATION BY INHALATION

CROSS REFERENCE TO RELEATED APPLICATIONS

This application is a continuation of U.S. patent application Ser. No. 14/417,484, filed on Jan. 26, 2015, which was a 371 application of International Patent Application No. PCT/EP2013/051187, filed on Jan. 23, 2013, and claims priority to European Patent Application No. 12152392.2, filed on Jan. 25, 2012.

TECHNICAL FIELD

The present invention relates to formulations for administration by inhalation by means of dry powder inhalers.

In particular, the invention relates to a dry powder formulation comprising a corticosteroid and a beta$_2$-adrenergic drug in combination, its process of preparation, and therapeutic uses thereof.

BACKGROUND OF THE INVENTION

Active substances commonly delivered by inhalation include bronchodilators such as beta-2 adrenoreceptor agonists and anticholinergics, corticosteroids, anti-allergies and other active ingredients that may be efficiently administered by inhalation, thus increasing the therapeutic index and reducing side effects of the active material.

Formoterol, i. e. 2'-hydroxy-5'-[(RS)-1-hydroxy-2{[(RS)-p-methoxy-α-methylphenethyl] amino} ethyl] formanilide, particularly its fumarate salt (hereinafter indicated as FF), is a well known beta-2 adrenergic receptor agonist, currently used clinically in the treatment of bronchial asthma, chronic obstructive pulmonary disease (COPD) and related disorders.

Beclometasone dipropionate (BDP) is a potent anti-inflammatory steroid, named (8S,9R,10S,11S,13S,14S,16S,17R)-9-chloro-11-hydroxy-10,13,16-trimethyl-3-oxo-17-[2-(propionyloxy)acetyl]-6,7,8,9,10,11,12,13,14,15,16,17-dodecahydro-3H-cyclopenta[a]phenanthren-17-yl propionate, available under a wide number of brands for the prophylaxis and/or treatment of inflammatory respiratory disorders.

A formulation for pressurized metered dose inhalers (pMDIs) containing both active ingredients in combination, both dissolved in a mixture of HFA134a and ethanol as co-solvent is currently on the market. It has been quoted in the literature as FF/BDP extra-fine formulation.

Said formulation provides a high lung deposition and uniform distribution throughout the bronchial tree, and is characterized by the fact that is capable of delivering a high fraction of particles having a diameter equal or less than 1.1 micron. In particular, upon actuation of the inhaler, it gives rise to a respirable fraction of about 40% and a fraction of particles having a diameter equal or less than 1.1 micron of about 12% for both active ingredients.

The major advantage of said formulation is related to the improved penetration into the bronchiole-alveolar distal part of the respiratory tree wherein inflammation is known to play a role in spontaneous exacerbations of asthma symptoms and wherein it is known that the density of the beta-2 adrenergic receptors is particularly high.

However, despite their popularity, pMDI formulation may have some disadvantages in particular in elderly and pediatric patients, mostly due to their difficulty to synchronize actuation from the device with inspiration.

Dry powder inhalers (DPIs) constitute a valid alternative to MDIs for the administration of drugs to airways.

On the other hand, drugs intended for inhalation as dry powders should be used in the form of micronised particles. Their volumetric contribution could represent an obstacle to design a formulation therapeutically equivalent to one wherein the drugs are delivered in form of liquid droplets.

WO 01/78693 discloses a dry powder formulation comprising formoterol and BDP in combination as active ingredient and, as a carrier, a fraction of coarse particles and a fraction made of fine excipient particles and magnesium stearate.

Upon its actuation, the respirable fraction of BDP is about 40%, while that of formoterol is about 47%.

More recently Mariotti et al (European Respiratory Society Annual Congress held in Amsterdam on Sep. 24-28, 2011), presented data about a FF/BDP dry powder formulation having a respirable fraction of about 70% for both active ingredients.

It is therefore an object of the invention to provide a powder formulation for DPIs comprising formoterol fumarate and BDP in combination, overcoming the problems indicated above and in particular to provide a powder formulation having therapeutic characteristics matching those of the corresponding pMDI formulation in form of solution.

The problem is solved by the formulation of the present invention.

SUMMARY OF THE INVENTION

The invention is directed to a dry powder formulation for use in a dry powder inhaler (DPI) comprising:
  a) a fraction of fine particles made of a mixture composed of 90 to 99.5 percent by weight of particles of a physiologically acceptable excipient and 0.5 to 10 percent by weight of magnesium stearate, said mixture having a mass median diameter lower than 20 micron;
  b) a fraction of coarse particles constituted of a physiologically acceptable excipient having a mass median diameter equal to or higher than 100 micron, wherein the ratio between the fine particles and the coarse particles being between 1:99 and 30:70 percent by weight; and
  c) formoterol fumarate dihydrate in combination with beclometasone dipropionate (BDP) as active ingredient both in form of micronized particles; wherein i) no more than 10% of said BDP particles have a diameter lower than 0.6 micron, ii) no more than 50% of said particles have a diameter comprised between 1.5 micron and 2.0 micron; and iii) at least 90% of said particles have a diameter lower than 4.7 micron.

In a second aspect, the invention is directed to a process for preparing the dry powder formulation of the invention comprising the step of mixing the carrier particles with the active ingredients.

In a third aspect, the invention concerns a dry powder inhaler filled with the above dry powder formulation.

In a fourth aspect, the invention refers to the claimed formulation for use in the prevention and/or treatment of an inflammatory or obstructive airways disease such as asthma or chronic obstructive pulmonary disease (COPD).

In a fifth aspect, the invention refers to a method of preventing and/or treating an inflammatory or obstructive airways disease such as asthma or chronic obstructive pulmonary disease (COPD), which comprises administering by inhalation an effective amount of the formulation of the invention.

In a sixth aspect, the invention refers to the use of the claimed formulation in the manufacture of a medicament for the prevention and/or treatment of an inflammatory or obstructive airways disease such as asthma or chronic obstructive pulmonary disease (COPD).

Definitions

By the term "physiologically acceptable" it is meant a safe pharmacologically-inert substance.

By "daily therapeutically effective dose" it is meant the quantity of active ingredient administered by inhalation upon actuation of the inhaler.

Said daily dose may be delivered in one or more actuations (shots or puffs) of the inhaler.

By the term "fine particles" it is meant particles having a size up to few tenths of microns.

By the term "micronized" it is meant a substance having a size of few microns.

By the term "coarse" it is meant particles having a size of one or few hundred microns.

In general terms, the particle size of particles is quantified by measuring a characteristic equivalent sphere diameter, known as volume diameter, by laser diffraction.

The particle size can also be quantified by measuring the mass diameter by means of suitable known instrument such as, for instance, the sieve analyser.

The volume diameter (VD) is related to the mass diameter (MD) by the density of the particles (assuming a size independent density for the particles).

In the present application, the particle size of the active ingredients is expressed in terms of volume diameter, while that of the excipient is expressed in terms of mass diameter.

The particles have a normal (Gaussian) distribution which is defined in terms of the volume or mass median diameter (VMD or MMD) which corresponds to the volume or mass diameter of 50 percent by weight of the particles, and, optionally, in terms of volume or mass diameter of 10% and 90% of the particles, respectively.

Another common approach to define the particle size distribution is to cite three values: i) the volume median diameter d(v,0.5) which is the volume diameter where 50% of the distribution is above and 50% is below; ii) d(v,0.9), where 90% of the volume distribution is below this value; iii) d(v,0.1), where 10% of the volume distribution is below this value. The span is the width of the distribution based on the 10%, 50% and 90% quantile and is calculated according to the formula.

$$\text{Span} = \frac{D[v, 0.9] - D[v, 0.1]}{D[v, 0.5]}$$

Upon aerosolisation, the particle size is expressed as mass aerodynamic diameter (MAD) and the particle size distribution as mass median aerodynamic diameter (MMAD). The MAD indicates the capability of the particles of being transported suspended in an air stream. The MMAD corresponds to the mass aerodynamic diameter of 50 percent by weight of the particles.

The term "hard pellets" refers to spherical or semispherical units whose core is made of coarse excipient particles.

The term "spheronisation" refers to the process of rounding off of the particles which occurs during the treatment.

The term "good flowability" refers to a formulation that is easy handled during the manufacturing process and is able to ensure an accurate and reproducible delivering of the therapeutically effective dose.

Flow characteristics can be evaluated by different tests such as angle of repose, Carr's index, Hausner ratio or flow rate through an orifice.

In the context of the present application the flow properties were tested by measuring the flow rate through an orifice according to the method described in the European Pharmacopeia (Eur. Ph.) 7.3, $7^{th}$ Edition.

The expression "good homogeneity" refers to a formulation wherein, upon mixing, the uniformity of distribution of the active ingredient, expressed as coefficient of variation (CV) also known as relative standard deviation (RSD), is less than 2.5%, preferably equal to or less than 1.5%.

The expression "respirable fraction" refers to an index of the percentage of active particles which would reach the deep lungs in a patient.

The respirable fraction, also termed fine particle fraction (FPF), is evaluated using a suitable in vitro apparatus such as Andersen Cascade Impactor (ACI), Multi Stage Liquid Impinger (MLSI) or Next Generation Impactor (NGI), preferably by ACI, according to procedures reported in common Pharmacopoeias, in particular in the European Pharmacopeia (Eur. Ph.) 7.3, $7^{th}$ Edition.

It is calculated by the percentage ratio between the fine particle mass (formerly fine particle dose) and the delivered dose.

The delivered dose is calculated from the cumulative deposition in the apparatus, while the fine particle mass is calculated from the deposition of particles having a diameter <5.0 micron.

The term "prevention" means an approach for reducing the risk of onset of a disease.

The term "treatment" means an approach for obtaining beneficial or desired results, including clinical results. Beneficial or desired clinical results can include, but are not limited to, alleviation or amelioration of one or more symptoms or conditions, diminishment of extent of disease, stabilized (i. e. not worsening) state of disease, preventing spread of disease, delay or slowing of disease progression, amelioration or palliation of the disease state, and remission (whether partial or total), whether detectable or undetectable. The term can also mean prolonging survival as compared to expected survival if not receiving treatment.

The term "coating" refers to the covering of the surface of the excipient particles by forming a thin film of magnesium stearate around said particles.

DETAILED DESCRIPTION OF THE INVENTION

The invention is directed to a dry powder formulation for use in a dry powder inhaler (DPI) comprising a fraction of fine particles a), a fraction of coarse particles b) and formoterol fumarate (FF) dihydrate in combination with beclometasone dipropionate (BDP) as active ingredients, having the characteristics disclosed herein.

The fractions a) and b) constitute the "carrier" particles.

It has been surprisingly found that in order to obtain a FF/BDP dry powder formulation therapeutically equivalent to the corresponding pMDI formulation currently on the market, it is necessary to generate a higher respirable fraction (FPF) as well as a higher fraction of particles having a diameter equal or less than 1.1 micron, for both the active ingredients.

It has also been found that this can be achieved by strictly controlling the particle size of the micronized BDP, and preferably its specific surface area.

Unexpectedly, it has been indeed further found that by setting the particle size distribution of BDP to the values herein claimed, not only its respirable fraction increases, but also that of formoterol fumarate (more than 60% vs about 47%).

Furthermore, the use of a micronized BDP characterized by such a selected, narrow, and well defined particle size distribution allows a better reproducibility of its fine particle fraction (FPF) during repeated administration.

The formulation according to the invention also shows a good homogeneity of the active ingredients, a good flowability and adequate physical and chemical stability in the inhaler before use for pharmaceutical purposes.

Advantageously, the fine and coarse excipient particles may be constituted of any physiologically acceptable material or combination thereof; preferred excipients are those made of crystalline sugars, in particular lactose; the most preferred are those made of α-lactose monohydrate.

Preferably, the coarse excipient particles and the fine excipient particles are both constituted of α-lactose monohydrate.

The fraction of fine particles a) must have a mass median diameter (MMD) lower than 20 micron, advantageously equal to or lower than 15 micron, preferably equal to lower than 10 micron, even more preferably equal to or lower than 6 micron.

Advantageously, the mass diameter of 90% of the fine particles a) is lower than 35 micron, more advantageously lower than 25 micron, preferably lower than 15 micron, even more preferably lower than 10 micron.

The ratio between the excipient particles and magnesium stearate within the fraction a) may vary depending on the doses of the active ingredients.

Advantageously, said fraction is composed of 90 to 99.5% by weight of the excipient and 0.5 to 10% by weight of magnesium stearate, preferably of 95 to 99% of the excipient, and 1 to 5% of magnesium stearate. A preferred ratio is 98% of the excipient and 2% of magnesium stearate.

Advantageously, at least 90% by weight of the particles of magnesium stearate has a starting mass diameter of not more than 35 micron and a MMD of not more than 15 micron, preferably not more than 10 micron.

Advantageously, magnesium stearate may coat the surface of the excipient particles in such a way that the extent of the surface coating is at least of 5%, preferably more than 10%, more preferably more than 15%, even more preferably equal to or more than 35%.

When the excipient particles are made of lactose, the extent of surface coating, which indicates the percentage of the total surface of the excipient particles coated by magnesium stearate, may be determined by water contact angle measurement, and then by applying the equation known in the literature as Cassie and Baxter, cited at page 338 of Colombo I et al *Il Farmaco* 1984, 39(10), 328-341 and reported below.

$$\cos \vartheta_{mixture} = f_{MgSt} \cos \vartheta_{MgSt} + f_{lactose} \cos \vartheta_{lactose}$$

where $f_{MgSt}$ and $f_{lactose}$ are the surface area fractions of magnesium stearate and of lactose;

$\vartheta_{MgSt}$ is the water contact angle of magnesium stearate;

$\vartheta_{lactose}$ is the water contact angle of lactose $\vartheta_{mixture}$ are the experimental contact angle values.

For the purpose of the invention, the contact angle may be determined with methods that are essentially based on a goniometric measurement. These imply the direct observation of the angle formed between the solid substrate and the liquid under testing. It is therefore quite simple to carry out, being the only limitation related to possible bias stemming from intra-operator variability. It should be, however, underlined that this drawback can be overcome by adoption of a fully automated procedure, such as a computer assisted image analysis. A particularly useful approach is the sessile or static drop method which is typically carried out by depositing a liquid drop onto the surface of the powder in form of disc obtained by compaction (compressed powder disc method).

The extent to which the magnesium stearate coats the surface of the excipient particles may also be determined by scanning electron microscopy (SEM), a well known versatile analytical technique.

Such microscopy may be equipped with an EDX analyzer (an Electron Dispersive X-ray analyzer), that can produce an image selective to certain types of atoms, for example magnesium atoms. In this manner it is possible to obtain a clear data set on the distribution of magnesium stearate on the surface of the excipient particles.

SEM may alternatively be combined with IR or Raman spectroscopy for determining the extent of coating, according to known procedures.

Another analytical technique that may advantageously be used is X-ray photoelectron spectroscopy (XPS), by which it has been possible to calculate both the extent of coating and the depth of the magnesium stearate film around the excipient particles.

The fraction of fine particles a) may be prepared according to one of the methods disclosed in WO 01/78693. Preferably, it could be prepared by co-micronization, more preferably using a ball mill. In some cases, co-milling for at least two hours may be found advantageous, although it will be appreciated that the time of treatment will generally depend on the starting particle size of the excipient particles and the desired size reduction to be obtained.

In a preferred embodiment of the invention the particles are co-micronised starting from excipient particles having a mass diameter less than 250 micron and magnesium stearate particles having a mass diameter less than 35 micron using a jet mill, preferably in inert atmosphere, for example under nitrogen.

As an example, alpha-lactose monohydrate commercially available such as Meggle D 30 or Spherolac 100 (Meggle, Wasserburg, Germany) could be used as starting excipient.

Optionally, the fraction of fine particles a) may be subjected to a conditioning step according to the conditions disclosed in the pending application n. WO 2011/131663.

The coarse excipient particles of the fraction b) must have a MMD of at least 100 micron, preferably greater than 125 micron, more preferably equal to or greater than 150 micron, even more preferably equal to or greater than 175 micron.

Advantageously, all the coarse particles have a mass diameter in the range 50-1000 micron, preferably comprised between 60 and 500 micron.

In certain embodiments of the invention, the mass diameter of said coarse particles might be comprised between 80 and 200 micron, preferably between 90 and 150 micron, while in another embodiment, the mass diameter might be comprised between 200 and 400 micron, preferably between 210 and 355 micron.

In a preferred embodiment of the invention, the mass diameter of the coarse particles is comprised between 210 and 355 micron.

In general, the person skilled in the art shall select the most proper size of the coarse excipient particles by sieving, using a proper classifier.

When the mass diameter of the coarse particles is comprised between 200 and 400 micron, the coarse excipient particles preferably have a relatively highly fissured surface, that is, on which there are clefts and valleys and other recessed regions, referred to herein collectively as fissures. The "relatively highly fissured" coarse particles can be defined in terms of fissure index or rugosity coefficient as described in WO 01/78695 and WO 01/78693, incorporated herein by reference, and they can be characterized according to the description therein reported. Said coarse particles may also be characterized in terms of tapped density or total intrusion volume measured as reported in WO 01/78695, whose teaching is incorporated herein by reference.

The tapped density of said coarse particles is advantageously less than 0.8 g/cm$^3$, preferably between 0.8 and 0.5 g/cm$^3$. The total intrusion volume is of at least 0.8 cm$^3$ preferably at least 0.9 cm$^3$.

The ratio between the fraction of fine particles a) and the fraction of coarse particles b) is comprised between 1:99 and 30:70% by weight, preferably between 2:98 and 20:80% by weight. In a preferred embodiment, the ratio is comprised between 10:90 and 15:85% by weight, even more preferably is of 10:90 by weight.

The step of mixing the coarse excipient particles b) and the fine particles a) is typically carried out in a suitable mixer, e.g. tumbler mixers such as Turbula™, rotary mixers or instant mixer such as Diosna™ for at least 5 minutes, preferably for at least 30 minutes, more preferably for at least two hours. In a general way, the person skilled in the art shall adjust the time of mixing and the speed of rotation of the mixer to obtain a homogenous mixture.

When spheronized coarse excipient particles are desired in order to obtain hard-pellets according to the definition reported above, the step of mixing shall be typically carried out for at least four hours.

All the micronized particles of beclometasone dipropionate (BDP) are characterized by a selected, narrow, and well defined particle size distribution in such a way that: i) no more than 10% of said particles have a diameter lower than 0.6 micron, preferably equal to or lower than 0.7 micron ii) no more than 50% of said particles have a diameter comprised between 1.5 micron and 2.0 micron, preferably between 1.6 and 1.9 micron; and iii) at least 90% of said particles have a diameter equal to or lower than 4.7 micron, preferably equal to or lower than 4.0 micron, more preferably equal to or lower than 3.8 micron.

The particular size distribution of BDP is characterized by: a d(v0.1) comprised between 0.8 and 1.0 micron, preferably between 0.85 and 0.95 micron; a d(v0.5) comprised between 1.5 and 2.0 micron preferably between 1.6 and 1.9 micron, a d(v0.9) comprised between 2.5 and 4.7 micron, preferably between 3.0 and 4.0 micron.

However the width of the particle size distribution of said BDP particles, expressed as a span, should be comprised between 1.2 and 2.2, preferably between 1.3 and 2.1, more preferably between 1.6 and 2.0, according the Chew et al J Pharm Pharmaceut Sci 2002, 5, 162-168, the span corresponds to [d(v,0.9)−d(v,0.1)]/d(v,0.5).

Advantageously, at least 99% of said particles [d(v,0.99)] have a diameter equal to or lower than 6.0 micron, and substantially all the particles have a volume diameter comprised between 6.0 and 0.4 micron, preferably between 5.5 and 0.45 micron.

The size of the particles active is determined by measuring the characteristic equivalent sphere diameter, known as volume diameter, by laser diffraction. In the reported examples, the volume diameter has been determined using a Malvern apparatus, However, other equivalent apparatus may be used by the skilled person in the art.

Advantageously, the micronized particles of BDP have also a specific surface area comprised between 5.5 and 7.0 m$^2$/g, preferably between 5.9 and 6.8 m$^2$/g. The Specific Surface Area is determined by Brunauer-Emmett-Teller (BET) nitrogen adsorption method according to a procedure known in the art.

All the micronized particles of formoterol fumarate dihydrate may have a diameter of less than 10 micron, preferably less than 6 micron. Advantageously at least 90% of the particles have a volume diameter lower than 5.0 micron. In a particular embodiment, the particle size distribution is such that: i) no more than 10% of the particles have a volume diameter lower than 0.8 micron, ii) no more than 50% of particles have a volume diameter lower than 1.7 micron; and iii) at least 90% of the particles have a volume diameter lower than 5.0 micron. Micronised formoterol fumarate dihydrate utilised in the formulation of the invention is also advantageously characterized by a Specific Surface Area comprised between 5 and 7.5 m$^2$/g, preferably between 5.2. and 6.5 m$^2$/g, more preferably between 5.5 and 5.8 m$^2$/g.

Both the micronised active ingredients utilized in the formulation of the invention may be prepared by grinding in a suitable mill. Preferably they are prepared by grinding using a conventional fluid energy mill such as commercially available jet mill micronizers having grinding chambers of different diameters. Depending on the type of the apparatus and size of the batch, the person skilled in the art shall suitably adjust the milling parameters such as the operating pressure, the feeding rate and other operating conditions to achieve the desired particle size.

In particular, to achieve the claimed particle size distribution of BDP, it is highly advantageous to utilize a jet mill micronizer having a grinding chamber of a diameter of 300 mm.

In a preferred embodiment, the invention is directed dry powder formulation for use in a dry powder inhaler (DPI) comprising:

a) a fraction of fine particles made of a mixture composed of 98 percent by weight of particles of alpha-lactose monohydrate and 2 percent by weight of magnesium stearate, said mixture having a mass median diameter equal to or lower than 6 micron;

b) a fraction of coarse particles constituted of alpha-lactose monohydrate having a mass diameter comprised between 212 and 355 micron and the ratio between the fine particles and the coarse particles being 10:90 percent by weight; and c) formoterol fumarate dihydrate in combination with beclometasone dipropionate (BDP) as active ingredient both in form of micronized particles; wherein i) no more than 10% of said BDP particles have a diameter [d(v,0.1)] lower than 0.7 micron, ii) no more than 50% of said particles have a diameter [d(v,0.5)] comprised between 1.6 micron and 1.9 micron; and iii) at least 90% of said particles have a diameter lower than 4.0 micron.

The present invention is also directed to a process for preparing the dry powder formulation disclosed herein comprising the step of mixing the fraction of fine particles a), the fraction of coarse particles b) with both the micronised active ingredients.

The carrier particles comprising the fraction of fine particles and the fraction of coarse particles may be prepared by mixing in suitable apparatus known to the skilled person, for example a Turbula™ mixer. The two fractions are preferably mixed in a Turbula™ mixer operating at a rotation speed of 16 r.p.m. for a period comprised between 30 and 300 minutes, preferably between 150 and 240 minutes.

The mixture of the carrier particles with the active ingredient particles may be carried out by mixing the components in suitable apparatus known to the skilled person, such as Turbula™ mixer for a period sufficient to achieve the homogeneity of the active ingredient in the final mixture, preferably comprised between 30 and 120 minutes, more preferably between 45 and 100 minutes.

Optionally, in an alternative embodiment, one active ingredient is first mixed with a portion of the carrier particles and the resulting blend is forced through a sieve, then, the further active ingredient and the remaining part of the carrier particles are blended with the sieved mixture; and finally the resulting mixture is sieved through a sieve, and mixed again.

The skilled person shall select the mesh size of the sieve depending on the particle size of the coarse particles.

The ratio between the carrier particles and the active ingredients will depend on the type of inhaler device used and the required dose.

Advantageously, the formulation of the invention may be suitable for delivering a therapeutic amount of both active ingredients in one or more actuations (shots or puffs) of the inhaler.

For example, the formulations will be suitable for delivering 6-12 μg formoterol (as fumarate dihydrate) per actuation, especially 6 μg or 12 μg per actuation, and 50-200 μg beclometasone dipropionate per actuation, especially 50, 100 or 200 μg per actuation.

The daily therapeutically effective dose may vary from 6 μg to 24 μg for formoterol and from 50 μg to 800 μg for BDP.

The dry powder formulation of the invention may be utilized with any dry powder inhaler.

Dry powder inhalers (DPIs) can be divided into two basic types: i) single dose inhalers, for the administration of single subdivided doses of the active compound; each single dose is usually filled in a capsule;

ii) multidose inhalers pre-loaded with quantities of active principles sufficient for longer treatment cycles.

Said dry powder formulation is particularly suitable for multidose DPIs comprising a reservoir from which individual therapeutic dosages can be withdrawn on demand through actuation of the device, for example that described in WO 2004/012801. Other multi-dose devices that may be used are for instance the DISKUS™ of GlaxoSmithKline, the TURBOHALER™ of AstraZeneca, TWISTHALER™ of Schering and CLICKHALER™ of Innovata. As marketed examples of single-dose devices, there may be mentioned ROTOHALER™ of GlaxoSmithKline and HANDIHALER™ of Boehringer Ingelheim.

In a preferred embodiment of the invention, the dry powder formulation is filled in the DPI disclosed in WO 2004/012801.

In case the ingress of moisture into the formulation is to be avoided, it may be desired to overwrap the DPI in a flexible package capable of resisting moisture ingress such as that disclosed in EP 1760008.

Administration of the formulation of the invention may be indicated for the prevention and/or treatment of a wide range of conditions including respiratory disorders such as chronic obstructive pulmonary disease (COPD) and asthma of all types and severity.

Other respiratory disorders characterized by obstruction of the peripheral airways as a result of inflammation and presence of mucus such as chronic obstructive bronchiolitis, and chronic bronchitis may also benefit by this kind of formulation.

The invention is illustrated in details by the following examples.

EXAMPLES

Example 1—Preparation of Different Batches of Micronised Particles of Beclometasone Dipropionate Different batches of beclometasone dipropionate were milled in a jet mill micronizer MC JETMILL® 300 (Jetpharma Sa, Switzerland) having a grinding chamber of a diameter of 300 mm.

The micronised batches were characterised in terms of particle size distribution and Specific Surface Area.

The particle size was determined by laser diffraction using a Malvern apparatus. The parameter taken into consideration was the VD in micron of 10%, 50% and 90% of the particles expressed as d(v,0.1), d(v, 0.5) and d(v, 0.9), respectively, which correspond to the mass diameter assuming a size independent density for the particles. The span [d(v,0.9)–d(v,0.1)]/d(v,0.5) is also reported. The Specific Surface Area (SSA) was determined by BET nitrogen adsorption using a Coulter SA3100 apparatus as a mean of three determinations.

The relevant data are reported in Table 1.

TABLE 1

Particle size distribution and Specific Surface Area (SSA) of different batches of micronised beclometasone dipropionate

| Particle size (μm) | Batch 1 | Batch 2 | Batch 3 | Batch 4 |
| --- | --- | --- | --- | --- |
| d (v, 0.1) | 0.86 | 0.96 | 0.95 | 0.91 |
| d (v, 0.5) | 1.63 | 1.81 | 1.71 | 1.84 |
| d (v, 0.9) | 3.15 | 3.33 | 2.97 | 3.76 |
| Span | 1.41 | 1.31 | 1.19 | 1.54 |
| SSA (m$^2$/g) | 6.61 | 5.90 | 6.12 | 6.28 |

Example 2—Preparation of the Fraction of Fine Particles a)

About 40 kg of co-micronised particles were prepared.

Particles of α-lactose monohydrate having a particle size of less than 250 micron (Meggle D 30, Meggle), and magnesium stearate particles having a particle size of less than 35 micron in a ratio 98:2 percent by weight were co-micronised by milling in a jet mill operating under nitrogen to obtain the fraction of fine particles a).

At the end of the treatment, said co-micronized particles have a mass median diameter (MMD) of about 6 micron.

Example 3—Preparation of the "Carrier" [Fraction a)+Fraction b)]

A sample of the fine particles of Example 1 were mixed with fissured coarse particles of α-lactose monohydrate having a mass diameter comprised between 212-355 micron, and obtained by sieving, in the ratio 90:10 percent by weight.

The mixing was carried out in a Turbula mixer operating at a rotation speed of 16 r.p.m. for a period of 240 minutes.

The resulting mixtures of particles, is termed hereinafter the "carrier".

Example 4—Preparation of the Dry Powder Formulation

A portion of the "carrier" as obtained in Example 3 was mixed with micronised formoterol fumarate dihydrate (FF) in a Turbula mixer for 30 minutes at 32 r.p.m. and the resulting blend was forced through a sieve with mesh size of 0.3 mm (300 micron).

Micronised beclometasone dipropionate (BDP) batch 1 or 4 as obtained in Example 1 and the remaining part of the "carrier" were blended in a Turbula mixer for 60 minutes at 16 r.p.m. with the sieved mixture to obtain the final formulation.

The ratio of the active ingredients to 10 mg of the "carrier" is 6 microg of FF dihydrate (theoretical delivered dose 4.5 microg) and 100 microg of BDP.

The powder formulations were characterized in terms of aerosol performances after loading it in the multidose dry powder inhaler described in WO 2004/012801.

The evaluation of the aerosol performance was carried out using the Andersen Cascade Impactor (ACI) according to the conditions reported in the European Pharmacopeia 6$^{th}$ Ed 2008, par 2.9.18, pages 293-295.

After aerosolization of 3 doses, the ACI apparatus was disassembled and the amounts of drug deposited in the stages were recovered by washing with a solvent mixture and then quantified by High-Performance Liquid Chromatography (HPLC). The following parameters, were calculated: i) the delivered dose which is the amount of drug delivered from the device recovered in the impactor; ii) the fine particle mass (FPM) which is the amount of delivered dose having a particle size equal to or lower than 5.0 micron; iii) the fine particle fraction (FPF) which is the percentage of the fine particle dose; iv) the MMAD.

The results (mean value±S.D) are reported in Table 2.

TABLE 2

Aerosol performances

| Sample | Batch 1 | Batch 4 |
|---|---|---|
| FF | | |
| Delivered Dose [μg] | 5.5 (±0.2) | 5.1 (±0.3) |
| Fine Particle Mass < 5 μm [μg] | 3.4 (±0.3) | 3.2 (±0.2) |
| Fine Particle Fraction < 5 μm [%] | 62.8 (±2.4) | 63.0 (±2.2) |
| Fine Particle Mass < 1 μm [μg] | 0.9 (±0.1) | 0.8 (±0.1) |
| Fine Particle Fraction < 1 μm [%] | 16.9 (±1.0) | 15.6 (±0.4) |
| MMAD [μm] | 1.69 (±0.0) | 1.75 (±0.0) |
| BDP | | |
| Delivered Dose [μg] | 89.8 (±3.7) | 88.2 (±3.5) |
| Fine Particle Mass [μg] | 54.0 (±4.0) | 52.4 (±2.9) |
| Fine Particle Fraction [%] | 60.1 (±2.3) | 59.4 (±1.8) |
| Fine Particle Mass < 1 μm [μg] | 24.2 (±2.5) | 23.1 (±1.7) |
| Fine Particle Fraction < 1 μm [%] | 26.9 (±1.9) | 26.2 (±1.2) |
| MMAD [μm] | 1.23 (±0.1)$^a$ | 1.25 (±0.1)$^a$ |

$^a$GSD which is the geometric standard deviation

From the data of Table 2, it can be appreciated that the formulations prepared using the micronized batches of BDP of Example 1 show a higher respirable fraction (FPF), for both the active ingredients (slightly more than 60%) than the corresponding pMDI formulation currently on the market (about 40%).

They also give rise to a higher fraction of particles having a diameter equal or less than 1.1 micron (more than 25% for both the active ingredients).

Example 5—Therapeutic Equivalence of FF/BDP Dry Powder Formulation of the Invention with the Corresponding pMDI Formulation Currently on the Market The study was designed to show that FF/BDP dry powder formulation delivered via the DPI disclosed in WO 2004/012801 is therapeutically equivalent to the corresponding pMDI formulation on the market.

Study Design:

A 5-way cross-over, double-blind, double-dummy clinical study.

69 asthmatic patients with $FEV_1$ 60% to 90% pred. were randomized. The 5 single doses tested were: 24/400 μg FF/BDP via DPI or pMDI, 6/100 μg FF/BDP via DPI or pMDI and placebo.

Primary Objective:

$FEV_1$ $AUC_{0-12h}$ which is the forced expiratory volume area under the curve for the time period 0 to 12 hours.

FEV1 is the maximal amount of air that can be forcefully exhaled in one second.

Results

For $FEV_1 AUC_{0-12h}$, non-inferiority between formulations was demonstrated with low dose and with high dose.

Both doses were significantly better than placebo. Superiority of high dose versus low dose was shown for both formulations on $FEV_1 AUC_{0-12h}$, reaching statistical significance for DPI. Safety and tolerability were good and comparable.

Example 6—Further Evidence of the Therapeutic Equivalence of FF/BDP Dry Powder Formulation of the Invention with the Corresponding pMDI Formulation Currently on the Market The aim of the study was to test the efficacy of 6/100 μg FF/BDP dry powder formulation delivered via the DPI (hereinafter FF/BDP DPI) disclosed in WO 2004/012801 versus the same dose of the corresponding pMDI formulation on the market (hereinafter FF/BDP pMDI) and the 100 μg BDP DPI formulation on the market (Clenil Pulvinal®, hereinafter BDP DPI).

Study Design:

A phase III, 8-week, multinational, multicentre, randomized, double-blind, triple-dummy, active controlled, 3-arm parallel-group clinical trial was carried out in adult asthmatic patients.

One inhalation twice daily of each formulation was administered for one month of treatment.

Primary Objective:

To demonstrate that FF/BDP DPI is non-inferior to FF/BDP pMDI in terms of change from baseline to the entire treatment period in average pre-dose morning peak expiratory flow (PEF).

PEF is a person's maximum speed of expiration, as measured with a peak flow meter, a small, hand-held device used to monitor a person's ability to breathe out air. It measures the airflow through the bronchi and thus the degree of obstruction in the airways.

Secondary Objectives:

To evaluate the superiority of FF/BDP DPI over BDP DPI in terms of change from baseline to the entire treatment period in average pre-dose morning PEF;

To evaluate the effect of FF/BDP DPI on other lung function parameters and on clinical outcome measures, and the safety and tolerability.

Results:

The non-inferiority of FF/BDP DPI relative to FF/BDP pMDI in terms of the primary efficacy variable has been demonstrated.

The same results as for pre-dose morning PEF have been obtained for pre-dose evening PEF No significant differences between treatments in terms of daily PEF variability have been observed The superiority over BDP DPI of both FF/BDP DPI and FF/BDP pMDI has also been demonstrated.

The FF/BDP DPI formulation turned out to be comparable to FF/BDP pMDI in terms of safety and tolerability.

The invention claimed is:

1. A dry powder formulation, comprising:
   a) a fraction of fine particles having a mass median diameter lower than 10 micron comprising particles of alpha-lactose monohydrate;
   b) a fraction of coarse particles constituted of alpha-lactose monohydrate having a mass diameter comprised between 60 and 500 micron and the ratio between the fine particles and the coarse particles being comprised between 1:99 and 30:70 percent by weight; and
   c) formoterol fumarate dihydrate in combination with beclometasone dipropionate (BDP) as active ingredient both in form of micronized particles; wherein i) no more than 10% of said BDP particles have a volume diameter lower than 0.6 micron, ii) no more than 50% of said particles have a volume diameter comprised between 1.5 micron and 2.0 micron; and iii) at least 90% of said particles have a volume diameter lower than 4.7 micron,
   wherein said formulation is contained in a dry powder inhaler and
   wherein said dry powder inhaler delivers formoterol fumarate dihydrate in a therapeutical dose of 6 or 12 μg, and BDP in a therapeutical dose of 100 or 200 μg per actuation of the inhaler; and whereby said formulation is therapeutically equivalent a formulation for pressurized metered dose inhalers (pMDIs) comprising the same amounts of BDP and formoterol fumarate dihydrate dissolved in a mixture of ethanol and HFA134a propellant.

2. The formulation, according to claim 1 wherein the d(v,0.1) of the BDP particles is comprised between 0.8 and 1.0 micron, the d(v0.5) is comprised between 1.5 and 2.0 micron, the d(v,0.9) is comprised between 2.5 and 4.7 micron and the particle size span, defined as [d(v,0.9)−d(v,0.1)]/d(v,0.5) is comprised between 1.2 and 2.2.

3. The formulation according to claim 2, wherein the BDP particles have a particle size span comprised between 1.3 and 2.1.

4. The formulation according to claim 1, wherein the BDP particles are further characterized by a specific surface area comprised between 5.5 and 7.0 $m^2/g$.

5. The formulation according to claim 4, wherein the specific surface area of the BDP particles is comprised between 5.9 and 6.8 $m^2/g$.

6. The formulation according to claim 1, wherein the ratio of fine particles a) and coarse particles b) is comprised between 2:98 and 20:80 percent by weight.

7. The formulation according to claim 6, wherein the ratio of fine particles a) and coarse particles b) is 10:90 percent by weight.

8. The formulation according to claim 1, wherein the coarse particles b) have a mass median diameter is comprised between 150 micron and 500 microns.

9. The formulation according to claim 8, wherein the mass diameter is comprised between 212 and 355 micron.

10. The formulation according to claim 1 constituted of:
    a) a fraction of fine particles made of a mixture composed of 98 percent by weight of particles of alpha-lactose monohydrate and 2 percent by weight of magnesium stearate, said mixture having a mass median diameter equal to or lower than 6 micron;
    b) a fraction of coarse particles constituted of alpha-lactose monohydrate having a mass diameter comprised between 212 and 355 micron and the ratio between the fine particles and the coarse particles being 10:90 percent by weight; and
    c) formoterol fumarate dihydrate in combination with beclometasone dipropionate (BDP) as active ingredient both in form of micronized particles; wherein i) no more than 10% of said BDP particles have a volume diameter lower than 0.7 micron, ii) no more than 50% of said particles have a volume diameter comprised between 1.6 micron and 1.9 micron; and iii) at least 90% of said particles have a volume diameter lower than 4.0 micron.

11. The formulation according to claim 1 for treatment of an inflammatory or obstructive airways disease.

12. The formulation according to claim 11, wherein the disease is asthma or chronic obstructive pulmonary disease (COPD).

* * * * *